United States Patent [19]

Hara et al.

[11] 4,269,926
[45] May 26, 1981

[54] STABILIZATION OF ORGANIC SUBSTRATE MATERIALS INCLUDING PHOTOGRAPHIC DYE IMAGES AGAINST THE ACTION OF LIGHT

[75] Inventors: Hiroshi Hara, Asaka; Kotaro Nakamura; Yoshiaki Suzuki, both of Minami-ashigara, all of Japan

[73] Assignee: Fuji Photo Film Co., Ltd., Minami-ashigara, Japan

[21] Appl. No.: 150,023

[22] Filed: May 15, 1980

Related U.S. Application Data

[62] Division of Ser. No. 29,085, Apr. 11, 1979.

[30] Foreign Application Priority Data

Apr. 17, 1978 [JP] Japan ................................. 53/45063

[51] Int. Cl.³ .................... G03C 1/40; G03C 1/84; G03C 1/10
[52] U.S. Cl. ...................... 430/216; 430/17; 430/211; 430/372; 430/512; 430/551; 430/559; 430/517
[58] Field of Search ............... 430/17, 216, 512, 518, 430/517, 551, 372, 211, 559; 260/45.75 C, 45.75 N, 45.75 R, 45.75 M; 8/74

[56] References Cited

U.S. PATENT DOCUMENTS 4,050,938  9/1977  Smith et al. ................... 430/170

OTHER PUBLICATIONS

Lendoy et al., *Inorganic Chem.*, vol. 7, No. 6, 6/1968, p. 1149.

*Primary Examiner*—Richard L. Schilling

*Attorney, Agent, or Firm*—Sughrue, Rothwell, Mion, Zinn and Macpeak

[57] ABSTRACT

A method of stabilizing an organic substrate material having an absorption maximum in the wavelength region of about 300 nm to about 800 nm to light without detracting from the color hue and the purity of the organic substrate material, which comprises making at least one metal complex salt represented by the following formula (I) coexist with the organic substrate material:

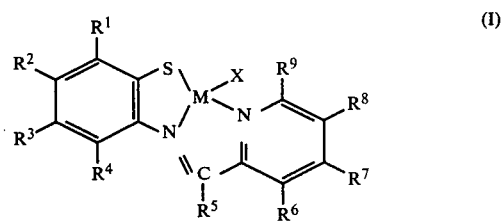

(I)

wherein M represents a Cu, Co, Ni, Pd or Pt atom; $R^1$, $R^2$, $R^3$, $R^4$, $R^6$, $R^7$, $R^8$ and $R^9$ each represents a hydrogen atom, a halogen atom or a cyano group, or an alkyl group, an aryl group, a cycloalkyl group or a heterocyclic ring which may be attached directly to the carbon atom in the respective ring or through a divalent coupling group, or $R^1$ and $R^2$, $R^2$ and $R^3$, $R^3$ and $R^4$, $R^6$ and $R^7$, $R^7$ and $R^8$, or $R^8$ and $R^9$ may combine to form the non-metal atoms necessary to complete a 6-membered ring; $R^5$ represents a hydrogen atom, an alkyl group or an aryl group; and X represents a chlorine atom, a bromine atom or an iodine atom.

2 Claims, No Drawings

STABILIZATION OF ORGANIC SUBSTRATE MATERIALS INCLUDING PHOTOGRAPHIC DYE IMAGES AGAINST THE ACTION OF LIGHT

This is a division of application Ser. No. 29,085 filed Apr. 11, 1979.

BACKGROUND OF THE INVENTION

1. Field of the Invention

The present invention relates to the stabilization of organic substrate materials to light and more particularly to the stabilization of organic compounds, particularly organic dyestuffs, to light.

2. Discussion of the Prior Art

In general, organic substrate materials, for instance, organic dyestuffs, tend to fade or to discolor upon exposure to light. A number of studies on the prevention of such fading or discoloration of organic dyestuffs, i.e., on improving light fastness, have been carried out in related technical fields including ink manufacture, textile dyeing, color photography and the like. The present invention is an effective method of improving the light fastness of organic substrate materials.

In the present specification, the term "organic substrate material" or "substrate material" includes substances which appear colored or colorless to the human eye under exposure to sunlight, that is, they include not only substances having absorption maxima in the visible region but also substances having absorption maxima in the near ultraviolet region, e.g., optical brightening agents, and further, substances having absorption maxima in the infrared region. Namely, in the present invention, organic substrate materials include organic substances having absorption maxima in the wavelength region of about 300 nm in the ultraviolet region to about 800 nm in infrared region.

These organic substrate materials occur particularly in photographic materials, e.g., color films, prints, diffusion transfer units, etc., in colored polymers useful as an agricultural vinyl cover sheets, umbrellas, tents, etc., fluorescent whitening agents, and dyed textiles, etc., and this invention is directed to improving the light fastness of these materials in each of these fields.

The term "dye" or "dyestuff" in the present specification includes an organic compound which appears colored to the human eye under exposure to sunlight.

The term "light" in the present specification includes electromagnetic radiation of wavelengths under about 800 nm, that is, it includes ultraviolet radiation under about 400 nm, visible light of about 400 nm to about 700 nm and infrared radiation of about 700 nm to about 800 nm.

The tendency for organic substrate materials, for instance, dyes or dyestuffs, to fade or to discolor upon optical exposure has long been known, and various methods for reducing fading or discoloration, that is, for improving the light fastness, have been proposed. For example, the fastness of an organic compound such as an indophenol, an indoaniline, an azo, an azomethine or like dyestuff to visible and ultraviolet light can be improved by mixing it with a phenolic compound having a fused heterocyclic system, as described in U.S. Pat. No. 3,432,300.

In the art of silver halide photographic light-sensitive materials, the oxidation products of an aromatic primary amine developing agent react with a color coupler to give rise to azomethine dyes or indoaniline dyes as described in C. E. K. Mees & T. H. James, *The Theory of the Photographic Process*, Chapter 17, Macmillan, New York (1967). A number of methods for improving the stability of images made up by such dyes, that is, color photographic images, are known. For example, the use of hydroquinone derivatives as fading or discoloration inhibitors as reported in U.S. Pat. Nos. 2,360,290, 2,418,613, 2,675,314, 2,701,197, 2,704,713, 2,728,659, 2,732,300, 2,735,765, 2,710,801 and 2,816,028, British Patent 1,363,921, etc., the use of gallic acid derivatives as reported in U.S. Pat. No. 3,457,079 and 3,069,262, Japanese Patent Publication is No. 13,496/68, etc., the use of p-alkoxyphenols as reported in U.S. Pat. Nos. 2,735,765 and 3,698,909, and the use of derivatives of chroman, coumaran and the like as reported in U.S. Pat. Nos. 3,432,300, 3,573,050, 3,574,627, 3,764,337, 3,574,626, 3,698,909 and 4,015,990, have been proposed. However, these derivatives do not effect sufficient fade or discoloration prevention.

In addition, another method in which the stability of organic substrate materials to light is improved by using azomethine quenching compounds having an absorption maxima in a wavelength region shifted to longer wavelengths than the absorption maxima of the substrate materials has been proposed in British Pat. No. 1,451,000. However, this method also suffers a disadvantage that the azomethine quenching compounds are per se intensely colored and, consequently, largely affect the hue of the substrate materials.

Moreover, by analogy to the prevention of photodeterioration of polymers utilizing metal complexes, as described in J. P. Guillory & R. S. Becker, *J. Polym. Sci., Polym. Chem. Ed.*, 12, 993 (1974) and R. P. R. Ranaweera & G. Scott, *J. Polym. Sci., Polym. Lett. Ed.*, 13, 71 (1975), still another method in which dyestuffs are stabilized by the addition of metal complexes has been reported in Japanese Patent Application (OPI) 87,649/75 (The term "OPI" as used herein refers to a "published unexamined Japanese patent application") and *Research Disclosure*, 15162 (1976). However, these complexes in themselves do not have a large fade preventing effect and additionally, they do not have a high solubility in common organic solvents. Therefore, they cannot be added in amounts necessary to exhibit a sufficient fade prevention effect. In addition, since these complexes per se are intensely colored, they suffer the disadvantage that their addition in large amounts adversely affects the color hue and the purity of the organic substrate materials and particularly dyestuffs.

SUMMARY OF THE INVENTION

Therefore, an object of the present invention is to provide a method for improving the stability of an organic substrate material to light.

Another object of the present invention is to provide a method of stabilizing an organic substrate material, and particularly, dyes or dyestuffs, to light without detracting from the hue and the purity of the organic substrate material.

A still another object of the present invention is to provide a method for improving the stability of an organic substrate material to light in which a particular stabilizer which has a high solubility in organic solvents and a high miscibility with the organic substrate material is employed for this end.

A further object of the present invention is to provide a method of improving the stability of a dye image constituting a color photographic image to light.

Another object of the present invention is to provide a method of improving the stability of dyestuffs produced by the reaction of an aromatic primary amine developing agent and a color photographic coupler to light.

Still another object of this invention is to improve the light fastness of colored polymers useful as agricultural vinyl sheets, umbrellas, tents, etc.

Other objects of the present invention will be apparent from the following description of the invention.

DETAILED DESCRIPTION OF THE INVENTION

The above-described objects and others are attained by making at least one compound of the formula (I) coexist with the organic substrate material having an absorption maximum in the wavelength region of about 300 nm to about 800 nm:

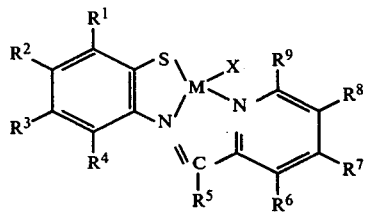

(I)

wherein M represents a Cu, Co, Ni, Pd or Pt atom; $R^1$, $R^2$, $R^3$, $R^4$, $R^6$, $R^7$, $R^8$ and $R^9$ each represents a hydrogen atom, a halogen atom (F, Cl, Br, I) or a cyano group, or an alkyl group, an aryl group, a cycloalkyl group or a heterocyclic ring which may be attached to the carbon atoms in the respective ring directly or through a divalent coupling group, or $R^1$ and $R^2$, $R^2$ and $R^3$, $R^3$ and $R^4$, $R^6$ and $R^7$, $R^7$ and $R^8$, or $R^8$ and $R^9$ may combine to form the non-metal atoms necessary to complete a 6-membered ring; $R^5$ represents a hydrogen atom, an alkyl group or an aryl group; and X represents a chlorine atom, a bromine atom or an iodine atom.

The terms "in the presence of" or "coexistant with" as used in the specification refer not only to the coexistence of the substrate material and the compound of the formula (I) in the same solution, dispersion, emulsion or layer, but also to the existence of the organic substrate material and the complex in, for example, adjacent layers of a multilayer photographic material. As long as the complex compound is associated with the organic substrate material such that it improves the light fastness of the organic substrate, it is used "in the presence of" or it "coexists with" the substrate for purposes of the present invention.

The alkyl groups represented by $R^1$, $R^2$, $R^3$, $R^4$, $R^6$, $R^7$, $R^8$ or $R^9$ include both substituted and unsubstituted alkyl groups containing preferably 1 to 20 carbon atoms excluding the carbon atoms contained in any substituent moiety. Further, the alkyl groups may be straight chain or branched chain. Examples of such alkyl groups include a methyl group, an ethyl group, a propyl group, a butyl group, an amyl group, a hexyl group, an octyl group, a decyl group, a hexadecyl group, a heptadecyl group, an octadecyl group and the like.

The cycloalkyl groups represented by $R^1$ to $R^4$ and $R^6$ to $R^9$ may contain 5 or 6 members, e.g., a cyclohexyl group or a cyclopentyl group.

Examples of aryl groups represented by $R^1$, $R^2$, $R^3$, $R^4$, $R^6$, $R^7$, $R^8$ and $R^9$ include both substituted and unsubstituted aryl groups preferably monocyclic or bicyclic aryl groups containing 6 to 14 carbon atoms excluding the carbon atoms contained in any substituent moiety. Representative examples include a phenyl group and a naphthyl group.

Examples of 6-membered rings formed by $R^1$ and $R^2$, $R^2$ and $R^3$, $R^3$ and $R^4$, $R^6$ and $R^7$, $R^7$ and $R^8$, or $R^8$ and $R^9$ include unsaturated 6-membered carbocyclic rings condensed with other rings (e.g., a naphthalene ring) and they may be substituted or unsubstituted. Specific examples of these 6-membered rings include a benzene ring and a naphthalene ring.

The heterocyclic group represented by $R^1$ to $R^4$ and $R^6$ to $R^9$ may be 5- or 6-membered rings containing at least one hetero atom selected from N, O and S, e.g., furyl, hydrofuryl, thienyl, pyrrolyl, pyrrolidyl, pyridyl, imidazolyl, pyrazolyl, quinolyl, indolyl, oxazolyl, thiazolyl, etc.

The alkyl groups, aryl groups, cycloalkyl groups or heterocyclic residues represented by $R^1$, $R^2$, $R^3$, $R^4$, $R^6$, $R^7$, $R^8$ or $R^9$ may be attached indirectly to the carbon atoms on their respective rings through divalent coupling group such as an oxy group (—O—), a thio group (—S—), an amino group, an oxycarbonyl group, a carbonyl group, a carbamoyl group, a sulfamoyl group, a carbonylamino group, a sulfonyl group, a carbonyloxy group or sulfonylamino group.

Examples of groups formed by alkyl groups represented by $R^1$, $R^2$, $R^3$, $R^4$, $R^6$, $R^7$, $R^8$ or $R^9$ in combination with the above-described divalent coupling groups through which the alkyl groups are to be attached to the carbon atoms on their respective rings include alkoxy groups (e.g., a methoxy group, an ethoxy group, a butoxy group, a propoxy group, an n-decyloxy group, an n-dodecyloxy group, an n-hexadecyloxy group, etc.), alkoxycarbonyl groups (e.g., a methoxycarbonyl group, an ethoxycarbonyl group, a butoxycarbonyl group, an n-decyloxycarbonyl group, an n-hexadecyloxycarbonyl group, etc.), acyl groups (e.g., an acetyl group, a valeryl group, a stearoyl group, a benzoyl group, a toluoyl group, etc.), acyloxy groups (e.g., an acetoxy group, a hexadecylcarbonyloxy group, etc.), alkylamino groups (e.g., an n-butylamino group, an N,N-diethylamino group, an N,N-didecylamino group, etc.), alkylcarbamoyl groups (e.g., a butylcarbamoyl group, an N,N-diethylcarbamoyl group, an n-dodecylcarbamoyl group, etc.), alkylsulfamoyl groups (e.g., a butylsulfamoyl group, an N,N-diethylsulfamoyl group, an N,N-diethylsulfamoyl group, an n-dodecylsulfamoyl group, etc.), sulfonylamino groups (e.g., a methylsulfonylamino group, a butylsulfonylamino group, etc.), sulfonyl groups (e.g., a mesyl group, an ethanesulfonyl group, etc.), acylamino groups (e.g., an acetylamino group, a valerylamino group, palmitoylamino group, etc.), and so on.

Examples of groups formed by cycloalkyl groups represented by $R_1$, $R_2$, $R_3$, $R_4$, $R_6$, $R^7$, $R^8$ or $R^9$ in combination with the above-described divalent coupling groups through which the cycloalkyl groups are attached to the carbon atoms on their respective rings include a cyclohexyloxy group, a cyclohexylcarbonyl group, a cyclohexyloxycarbonyl group, a cyclohexylamino group, and the like.

Examples of groups formed by aryl groups represented by $R_1$, $R^2$, $R^3$, $R^4$, $R^6$, $R^7$, $R^8$ or $R^9$ in combination with the above-described divalent coupling groups, through which the aryl groups are attached to the carbon atoms on their respective rings, include aryloxy groups (e.g., a phenoxy group, a naphthoxy group, etc.), aryloxycarbonyl groups (e.g., a phenoxycarbonyl group, a naphthoxycarbonyl group, etc.), acyl groups (e.g., a benzoyl group, a naphthoyl group, etc.), anilino groups (e.g., a phenylamino group, an N-methylanilino group, an N-acetylanilino group, etc.), acyloxy groups (e.g., a benzoyloxy group, a toluoyloxy group, etc.), arylcarbamoyl groups (e.g., a phenylcarbamoyl group, etc.), arylsulfamoyl group (e.g., a phenylsulfamoyl group, etc.), arylsulfonylamino groups (e.g., a phenylsulfonylamino group, a p-tolylsulfonylamino group, etc.), arylsulfonyl groups (e.g., a benzenesulfonyl group, a tosyl group, etc.) and acylamino groups (e.g., a benzoylamino group, a toluoylamino group, etc.).

Alkyl groups represented by $R^1$, $R^2$, $R^3$, $R^4$, $R^6$, $R^7$, $R^8$ or $R^9$, aryl groups represented by $R^1$, $R^2$, $R^3$, $R^4$, $R^6$, $R^7$, $R^8$ or $R^9$, and 6-membered rings formed by combining $R^1$ and $R^2$, $R^2$ and $R^3$, $R^3$ and $R^4$, $R^6$ and $R^7$, $R^7$ and $R^8$, or $R^8$ and $R^9$ may be substituted by a halogen atom (e.g., chlorine, bromine, fluorine, etc.), a cyano group, a $C_1$–$C_{20}$ alkyl group (e.g., a methyl group, an ethyl group, a propyl group, a butyl group, a hexyl group, an octyl group, a decyl group, a dodecyl group, a tetradecyl group, a hexadecyl group, a heptadecyl group, an octadecyl group, a methoxyethoxyethyl group, etc.), a $C_6$–$C_{14}$ aryl group (e.g., a phenyl group, a tolyl group, a naphthyl group, a chlorophenyl group, a methoxyphenyl group, an acetylphenyl group, etc.), a $C_7$–$C_{30}$ aralkyl group (e.g., a benzyl group, a 6-phenylhexyl group, an anisyl group, etc.), a $C_2$–$C_{20}$ acyloxy group (e.g., an acetoxy group, a benzoyloxy group, a p-methoxybenzoyloxy group, etc.), a $C_1$–$C_{20}$ alkoxy group (e.g., a methoxy group, an ethoxy group, a butoxy group, a propoxy group, a methoxyethoxy group, etc.), a $C_6$–$C_{14}$ aryloxy group (e.g., a phenoxy group, a tolyloxy group, a naphthoxy group, a methoxyphenoxy group, etc.), an alkoxycarbonyl group having 1 to 20 carbon atoms in the alkyl moiety (e.g., a methoxycarbonyl group, a butoxycarbonyl group, a phenoxymethoxycarbonyl group, etc.), an aryloxycarbonyl group having 6 to 14 carbon atoms in the aryl moiety (e.g., a phenoxycarbonyl group, a tolyoxycarbonyl group, a methoxyphenoxycarbonyl group, etc.), a $C_2$–$C_{20}$ acyl group (e.g., a formyl group, an acetyl group, a valeryl group, a stearoyl group, a benzoyl group, a toluoyl group, a naphthoyl group, a p-methoxybenzoyl group, etc.), a $C_2$–$C_{20}$ acylamino group (e.g., an acetamido group, a benzamido group, a methoxyacetamido group, etc.), an anilino group including an N-($C_1$-$C_{20}$) alkylanilino group (e.g., a phenylamino group, an N-methylanilino group, an N-phenylanilino group, an N-acetylanilino group, etc.), a $C_1$-$C_{20}$ alkylamino group (e.g., an n-butylamino group, an N,N-diethylamino group, a 4-methoxy-n-butylamino group, etc.), a carbamoyl group including an alkylcarbamoyl group having 1 to 20 carbon atoms in the alkyl moiety (e.g., an n-butylcarbamoyl group, etc.), a sulfamoyl group including an alkylsulfamoyl group having 1 to 20 carbon atoms in the alkyl moiety (e.g., an N,N-diethylsulfamoyl group, an n-dodecylsulfamoyl group, an N-(4-methoxy-n-butyl)-sulfamoyl group, etc.), a sulfonylamino group including an alkylsulfonylamino group having 1 to 20 carbon atoms in the alkyl moiety (e.g., a methylsulfonylamino group, a phenylsulfonylamino group, a methoxymethylsulfonylamino group, etc.), a sulfonyl group including an alkylsulfonyl group having 1 to 20 carbon atoms in the alkyl moiety (e.g., a mesyl group, a tosyl group, a methoxymethanesulfonyl group, etc.), etc.

Alkyl groups represented by $R^5$ include both substituted and unsubstituted alkyl groups which may be straight chain or branched chain. These alkyl groups preferably have 1 to 20 carbon atoms excluding the carbon atoms in any substituent moiety with examples including a methyl group, an ethyl group, a propyl group, a butyl group, a hexyl group, an octyl group, a decyl group, a dodecyl group, a tetradecyl group, a hexadecyl group, a heptadecyl group, an octadecyl group, etc.

Aryl groups represented by $R^5$ include both substituted and unsubstituted mono- and bicyclic aryl groups having preferably 6 to 14 carbon atoms excluding the carbon atoms in any substituent moiety. Representative examples include a phenyl group, a tolyl group, a naphthyl group, etc.

Alkyl groups or aryl groups represented by $R^5$ may be substituted by the same substituents as cited for the alkyl groups or aryl groups, respectively, represented by $R^1$, $R^2$, $R^3$, $R^4$, $R^6$, $R^7$, $R^8$ or $R^9$.

X represents a chlorine atom, a bromine atom or an iodine atom.

Of compounds represented by the general formula (I), compounds which are preferably employed in the present invention can be represented by the formula (Ia):

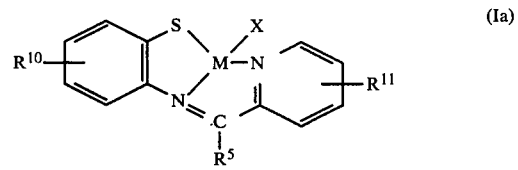

wherein M represents Cu, Co, Ni, Pd or Pt; $R^{10}$ and $R^{11}$ each represents a hydrogen atom, a halogen atom (e.g., a chlorine atom, a bromine atom, a fluorine atom, etc.), a cyano group, or an alkyl group, an aryl group, a cycloalkyl group or a heterocyclic ring each of which is attached to the carbon atom on its respective ring directly or indirectly via a divalent coupling group; $R^5$ represents a hydrogen atom, an alkyl group or an aryl group; and X represents a chlorine atom, a bromine atom or an iodine atom.

Therein, $R^{10}$ and $R^{11}$ are represented by the same substituents as defined above for $R^1$, $R^2$, $R^3$, $R^4$, $R^6$, $R^7$, $R^8$ or $R^9$ of the general formula (I).

Halogen atoms represented by X include a chlorine atom, a bromine atom and an iodine atom.

Compounds particularly effective in the practice of the present invention, which are within the scope of the above-described general formula (I), are those which have structural formulae as illustrated below. However, these compounds are provided here for illustration only and the present invention is not intended to be construed as being limited to these compounds.

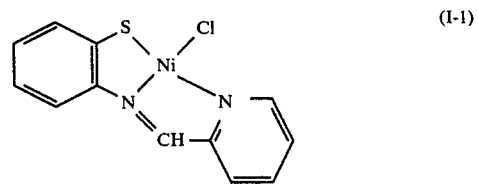

(I-1)

-continued
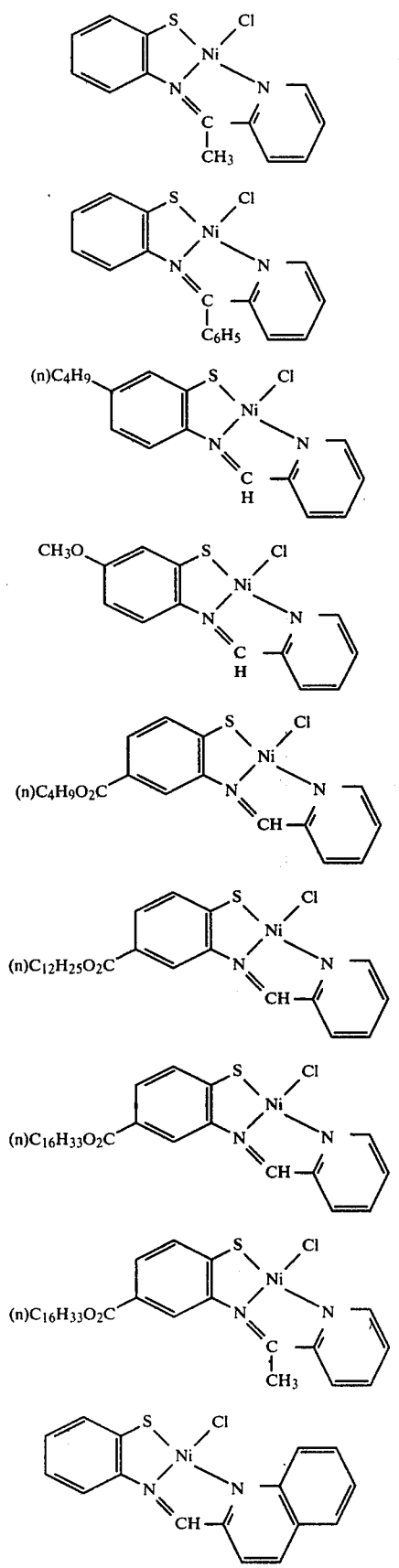
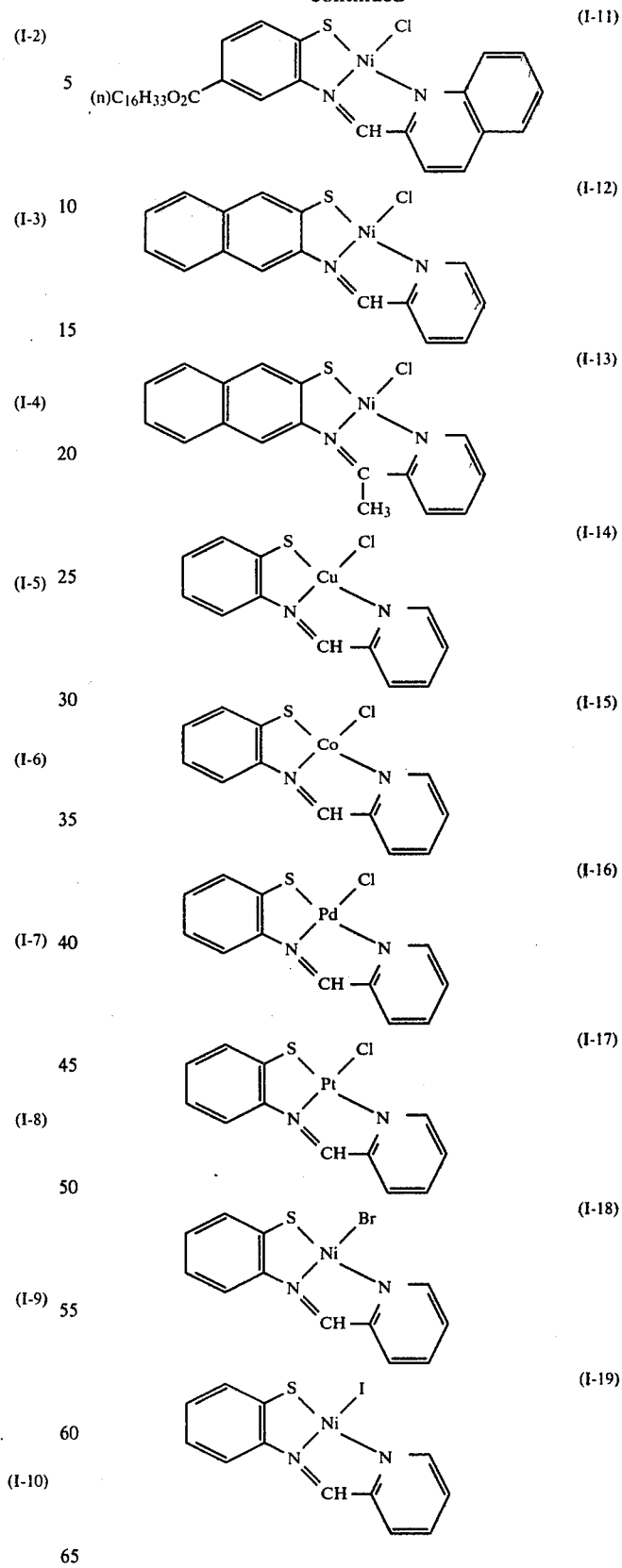
Methods for synthesizing the above-illustrated complexes are described, for example, in L. F. Lindoy & S. E. Livingstone, *Inorg. Chem.*, Volume 7, p. 1149 (1968).

A 2-(2-pyridyl)benzothiazoline derivative is refluxed in a lower alcohol in an inert gas such as nitrogen. An alcoholic solution of a metal salt such as nickel chloride is slowly added to the mixture. After further refluxing with stirring, the resulting mixture is allowed to stand at room temperature. The crystals which precipitate are purified in a conventional manner.

SYNTHESIS EXAMPLE 1

Synthesis of Compound I-1

Under an atmosphere of nitrogen gas, 4.3 g of 2-(2-pyridyl)benzothiazoline (prepared by reacting an o-aminobenzenethiol with a (2-pyridine)carboxyaldehyde in ethanol at room temperature and purifying the product in a conventional manner) was dissolved in one liter of ethanol and refluxed. Thereto, a solution prepared by dissolving 4.8 g of nickel chloride hexahydrate in 1 liter of ethanol was added dropwise over about 1 hour. After completion of dropwise addition, the refluxing was continued for an additional 10 minutes. Then, the reaction mixture was cooled to room temperature. Thereupon, a reddish brown solid precipitated. The precipitate was washed with chilled ethanol and dried. The crude product was recrystallized from a mixed solvent consisting of methylene chloride and n-hexane.

SYNTHESIS EXAMPLE 2

Synthesis of Compound I-6

Under an atmosphere of nitrogen gas, 6.2 g of 2-(2-pyridyl)-5-(n-butoxycarbonyl)benzothiazoline was dissolved in 1 liter of ethanol and refluxed. Thereto, a solution prepared by dissolving 4.8 g of nickel chloride hexahydrate in 1 liter of ethanol was added dropwise over about 1 hour. After completion of the addition, the refluxing was continued for an additional 10 minutes. The solvent of the reaction mixture was removed by distillation. The thus-obtained solid was recrystallized from a mixed solvent of methylene chloride and n-hexane.

As will be apparent from the extensive discussion and examples of the organic substrate which follows, the present invention is effective with a very wide variety of organic materials, the essential point being that the substrate materials have a maximum absorption wavelength in the range of 300 to 800 nm.

The organic substrate materials in this invention include all dyes belonging to the following classes based on dyeing property, i.e., water-soluble dyes such as basic dyes, acid dyes, direct dyes, soluble vat dyes, mordant dyes, etc.; water-insoluble dyes such as sulfur dyes, vat dyes, oil colors, disperse dyes, azoic dyes, acid dyes, etc.; and reactive dyes. These organic substrate materials include not only the dyes which are seen as colored materials under sunlight but also colorless or light yellow optical whitening dyes.

Of these dyes, the dyes preferably used in conjunction with this invention are quinoneimine dyes (e.g., azine dyes, oxazine dyes, thiazine dyes, etc.), methine and polymethine dyes (e.g., cyanine dyes, azomethine dyes, etc.), azo dyes, anthraquinone dyes, indoamine dyes, indophenol dyes, indigoid dyes, carbonium dyes, formazan dyes, etc., classified by chemical structure.

The organic substrate materials in this invention also include image-forming dyes used in the field of photography, for example, the dyes formed from color couplers, DRR compounds, DDR couplers, amidrazone compounds, dye developers, etc., and dyes for the silver dye bleach process.

Preferred organic substrate materials in this invention are anthraquinone dyes, quinoneimine dyes, azo dyes, methine dyes, polymethine dyes, indoamine dyes, indophenol dyes, and formazan dyes.

Furthermore, examples of the most preferred dyes used at the practice of this invention are methine dyes, polymethine dyes, indoamine dyes and indophenol dyes. The methine dyes, polymethine dyes, indoamine dyes, and indophenol dyes also include compounds having the following moiety

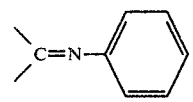

wherein the phenyl group may be substituted by an alkyl group, an alkoxy group, a halogen atom, or an amino group.

The dye-forming couplers suitably used in this invention include yellow dye-forming couplers, magenta dyeforming couplers and cyan dye-forming couplers. These couplers may be so-called 4-equivalent couplers or 2-equivalent couplers as described in U.S. Pat. Nos. 3,277,155 and 3,458,315.

The yellow dye-forming couplers generally contain at least one methylene group activated by a carbonyl group (for example, open chain type ketomethylene groups) and include β-diketones and β-ketoacylamides such as, for example, benzylacetanilide and α-pivalylacetanilide. Examples of the suitable yellow couplers used in this invention are described in U.S. Pat. Nos. 2,428,054, 4,026,706, 2,499,966, 2,453,661, 2,778,658, 2,908,573, 3,227,550, 3,253,924, 3,277,155 and 3,384,657 and British Pat. No. 503,752.

As the magenta dye-forming couplers used in this invention, there are, for example, 5-pyrazolone type couplers. The couplers of this type are described in, for example, U.S. Pat. Nos. 2,600,788, 2,725,292, 2,908,573, 3,006,759, 3,062,653, 3,152,896, 3,227,550, 3,252,924, 4,026,706 and 3,311,476.

Other magenta dye-forming couplers used in this invention are the indazolones of the type as described in Vittum and Weissberger, *Journal of Photographic Science*, Vol. 6, page 158 et seq. (1958) and practical examples of such magenta dye-forming couplers are pyrazolinobenzimidazole as described in U.S. Pat. No. 3,061,432, pyrazolo-s-triazole as described in Belgian Pat. No. 724,427, and 2-cyanoacetylcumarone as described in U.S. Pat. No. 2,115,394.

The cyan dye-forming couplers which can be used in this invention include phenol compounds and α-naphthol compounds. The compounds of this type are illustrated in U.S. Pat. Nos. 2,275,292, 2,423,730, 2,474,293, 2,895,826, 2,908,573, 3,043,892, 4,026,706, 3,227,550 and 3,253,294.

In general, the couplers described above are further described in, for example, Kirk-Othmer, *Encyclopedia of Chemical Technology*, Vol. 5, pp. 822–825 and Glafkides, *Photographic Chemistry*, Vol. 2, pp. 596–614.

As described above, when such couplers are used in the practice of this invention, dyes are formed by the reaction of these couplers and an oxidized aromatic primary amino silver halide developing agent.

The developing agent described above includes an aminophenol and a phenylenediamine and they may include a mixture of them.

Typical examples of the developing agent which can form the organic substrate materials by combining various couplers are illustrated as follows:

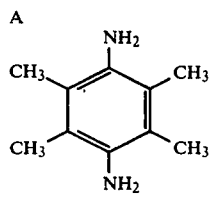
A

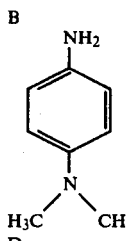
B

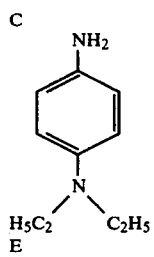
C

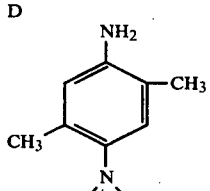
D

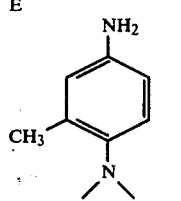
E

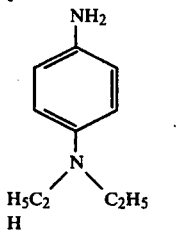
F

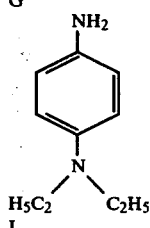
G

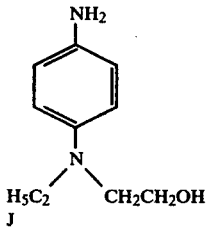
H

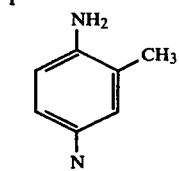
I

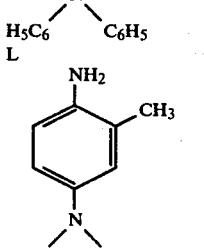
J

K

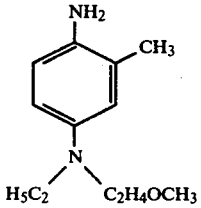
L

Representative examples of the developing agents capable of forming the base compounds by coupling into various kinds of couplers according to an embodiment of the present invention are p-phenylenediamines and the derivatives thereof as described in T. H. James, *The Theory of the Photographic Process*, the fourth edition, pp. 315–320, Macmillan, New York (1977). Preferred p-phenylenediamines or the derivatives thereof are p-phenylenediamines in which at least one amino group is substituted by lower alkyl group(s) having 1 to 3 carbon atoms and the derivative thereof, for example, 4-amino-N,N-dimethylaniline, 4-amino-N,N-diethylaniline, 4-amino-3-methyl-N,N-diethylaniline, 4-amino-3-ethyl-N-ethyl-N-(β-methanesulfonamidoethyl)aniline, 4-amino-N-ethyl-N-(β-hydroxyethyl)aniline, 4-amino-3-methyl-N-ethyl-N-(β-hydroxyethyl)aniline and so on.

Cyan, magenta and yellow couplers which are preferably employed are represented by the formulae (II), (III) or (IV) below, respectively:

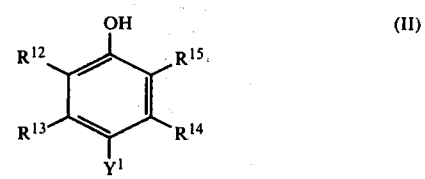

(II)

wherein $R^{12}$, $R^{13}$, $R^{14}$ and $R^{15}$ each represents a hydrogen atom, a halogen atom (e.g., fluorine, chlorine, bromine or iodine), an alkyl group having 1 to 20 carbon atoms (e.g., methyl, ethyl, octyl, dodecyl, tetradecyl, octadecyl, etc.); an alkyl- or aryl-substituted carbamoyl wherein the aryl moiety has 6 to 10 carbon atoms (e.g., methylcarbamoyl, ethylcarbamoyl, dodecylcarbamoyl, tetradecylcarbamoyl, octadecylcarbamoyl, N-phenylcarbamoyl, N-tolylcarbamoyl, etc.); an alkyl- or aryl-substituted sulfamoyl group (e.g., methylsulfamoyl, ethylsulfamoyl, dodecylsulfamoyl, tetradecylsulfamoyl, octadecylsulfamoyl, N-phenylsulfamoyl, N-tolylsulfamoyl, etc.); an alkyl- or aryl-substituted amido group (e.g., acetamido, butylamido, benzamido, phenacetamido, etc.); a sulfonamido group (e.g., benzenesulfonamido), a phosphoric acid amido group, a ureido group, etc.

$R^{12}$ and $R^{13}$ may combine with each other to form a 6-membered carbocyclic ring (e.g., a benzene ring which may further be substituted with a $C_1$–$C_{20}$ alkyl or $C_6$–$C_{14}$ aryl group).

$Y^1$ represents a hydrogen atom, a halogen atom (e.g., fluorine, chlorine, bromine or iodine); or a group which is releasable upon the reaction with the oxidation product of a developing agent (e.g., an alkoxy group wherein the alkyl moiety has 1 to 20 carbon atoms; an aryloxy group wherein the aryl moiety has 6 to 10 carbon atoms; a sulfonamido group, a sulfonyl group, a carbamoyl group, an imido group, an aminosulfonyloxy group, an alkylcarbonyloxy group, an arylcarbonyloxy group, an alkylthio group, an arylthio group, a heterocyclic ring thio group, etc.; the details of which are well known in the art.

The alkyl, carbamoyl, sulfamoyl and amido groups expressed by $R^{12}$, $R^{13}$, $R^{14}$ and $R^{15}$, or the 6-membered ring formed by combining $R^{12}$ and $R^{13}$ with each other can also be substituted with other substituents, for example, a $C_1$–$C_{20}$ alkyl group (e.g., methyl, ethyl, propyl, octyl, dodecyl, tetradecyl, octadecyl, etc.); a $C_6$–$C_{14}$ aryl group (e.g., phenyl, tolyl, naphthyl, etc.); a $C_6$–$C_{14}$ aryloxy group (e.g., phenoxy, 2,5-di(t)-amylphenoxy, etc.); a halogen atom (e.g., chlorine, bromine, fluorine, etc.); and the like.

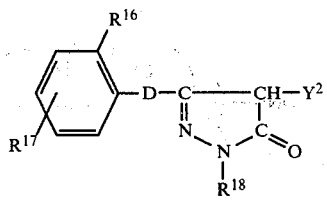

wherein $R^{16}$ represents a hydrogen atom, a halogen atom (e.g., chlorine, bromine, fluorine, etc.); a $C_1$-$C_{20}$ alkyl group (e.g., methyl, ethyl, n-propyl, etc.); or a $C_1$-$C_{20}$ alkoxy group (e.g., methoxy, ethoxy, etc.); $R^{17}$ represents a $C_1$-$C_{20}$ alkyl group (e.g., methyl, ethyl, octyl, dodecyl, tetradecyl, octadecyl, etc.); an amido group (e.g., butanamido, decanamido, tetradecanamido, nonadecanamido, etc.); an imido group (e.g., tetradecylsuccinimido, octadecenylsuccinimido, etc.); an N-alkylcarbamoyl group the alkyl moiety of which contains 1 to 20 carbon atoms (e.g., decylcarbamoyl, tetradecylcarbamoyl, octadecylcarbamoyl, etc.); an N-alkylsulfamoyl group the alkyl moiety of which contains 1 to 20 carbon atoms (e.g., decylsulfamoyl, tetradecylsulfamoyl, octadecylsulfamoyl, etc.); an alkoxycarbonyl group the alkyl moiety of which contains 1 to 20 carbon atoms (e.g., decyloxycarbonyl, tetradecyloxycarbonyl, octadecyloxycarbonyl, etc.); an acyloxy group (e.g., valeryloxy, palmitoyloxy, stearoyloxy, oleyloxy, benzoyloxy, toluoyloxy, etc.); a sulfonamido group, a urethane group, etc.; and $R^{18}$ represents a $C_6$-$C_{14}$ aryl group (e.g., phenyl, naphthyl, etc.), said alkyl and aryl groups having 1 to 20 and 6 to 14 carbon atoms, respectively.

D represents an amino group, a carbonylamino group, or a ureido group.

$Y^2$ represents a hydrogen atom, a halogen atom (e.g., chlorine, bromine, etc.); or a group which is releasable upon reaction with the oxidation product of a developing agent (e.g., an arylazo group, an aryloxy group, an acyloxy group, an alkylthio group, an arylthio group, etc.). Such groups are well known.

The alkyl or alkoxy group represented by $R^{16}$, the alkyl, amido, N-alkylcarbamoyl, N-alkylsulfamoyl, alkoxycarbonyl or acyloxy group represented by $R^{17}$, or the aryl group represented by $R^{18}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a halogen atom (e.g., chlorine, bromine, fluorine, etc.), or the like.

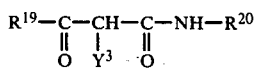

wherein $R^{19}$ represents a $C_1$-$C_{20}$ alkyl group (e.g., methyl, ethyl, (t)-butyl, (t)-octyl, etc.) or a $C_6$-$C_{14}$ aryl group (e.g., phenyl) and $R^{20}$ represents a $C_6$-$C_{14}$ aryl group (e.g., phenyl).

$Y^3$ represents a hydrogen atom, a halogen atom (e.g., chlorine, bromine, etc.), or a group which is releasable upon reaction with the oxidation product of a developing agent, for example, a heterocyclic nuclei (e.g., naphthoimido, succinimido, 5,5-dimethylhydantoinyl, 2,4-oxazolidinedione residue, imido, pyridone residue, pyridazone residue, etc.), an acyloxy group, a sulfonyloxy group, an aryloxy group, a ureido group, which are well known in the art.

The alkyl or aryl group represented by $R^{19}$ and the aryl group represented by $R^{20}$ can also be substituted with other substituents, for example, an alkyl group, an aryl group, an alkoxy group, an aryloxy group, an amido group, an N-alkylcarbamoyl group, an N-alkylsulfamoyl group, an acyloxy group, a carboxy group, a sulfo group, a sulfonamido group, a halogen atom, etc., the alkyl and aryl moieties of which contain 1 to 20 and 6 to 14 carbon atoms, respectively.

Then, practical examples of the couplers which can form organic substrate materials by the reaction with the aforesaid or other developing agents are as follows:

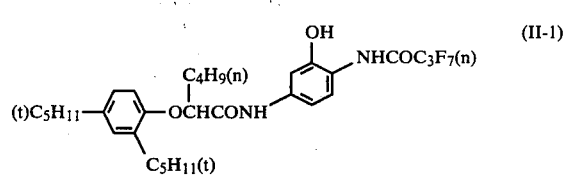

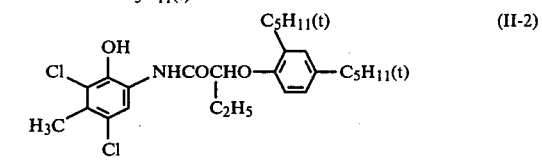

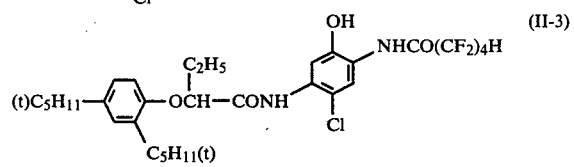

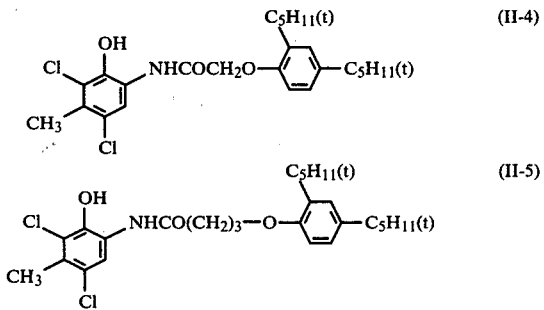

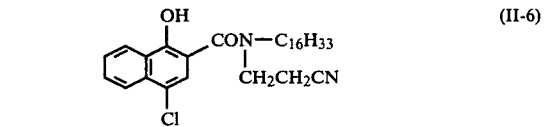

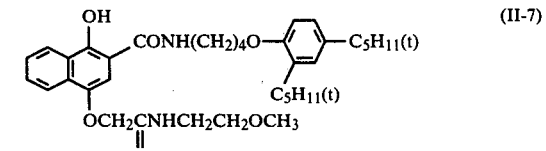

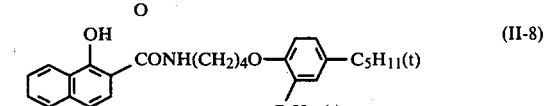

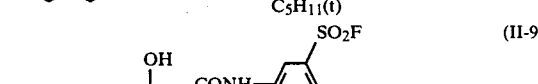

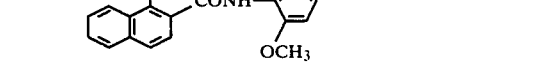

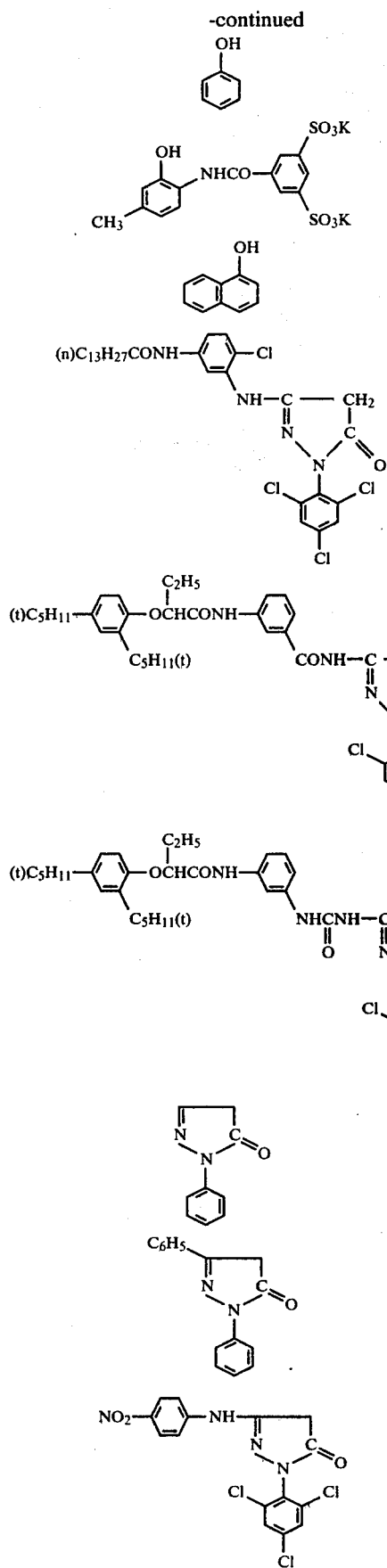
Specific examples of other dyestuffs or compounds capable of forming them which can be employed as the base compounds in the practice of the present invention are illustrated below.

-continued
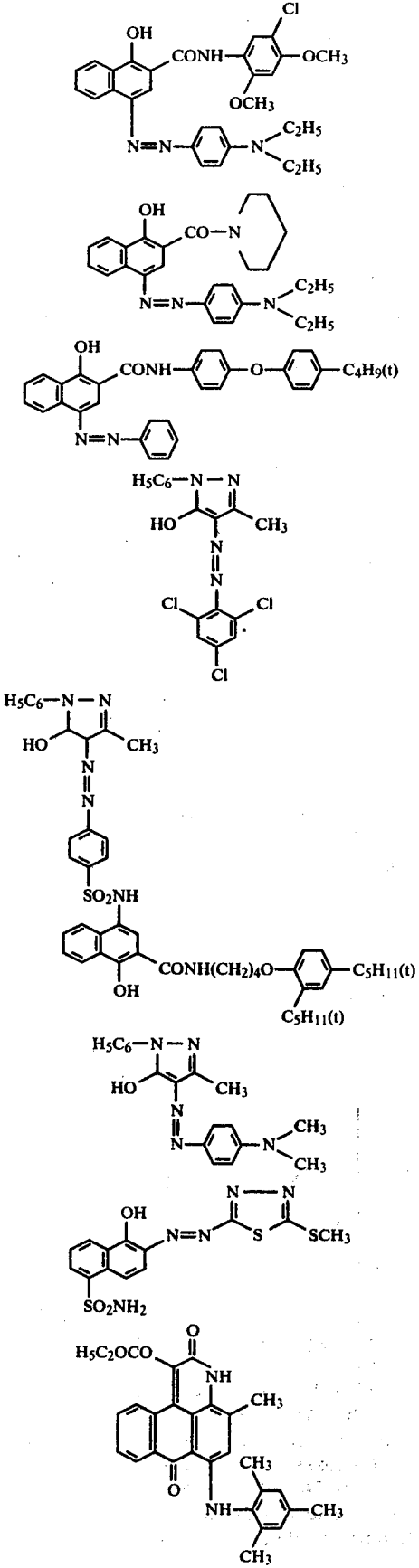
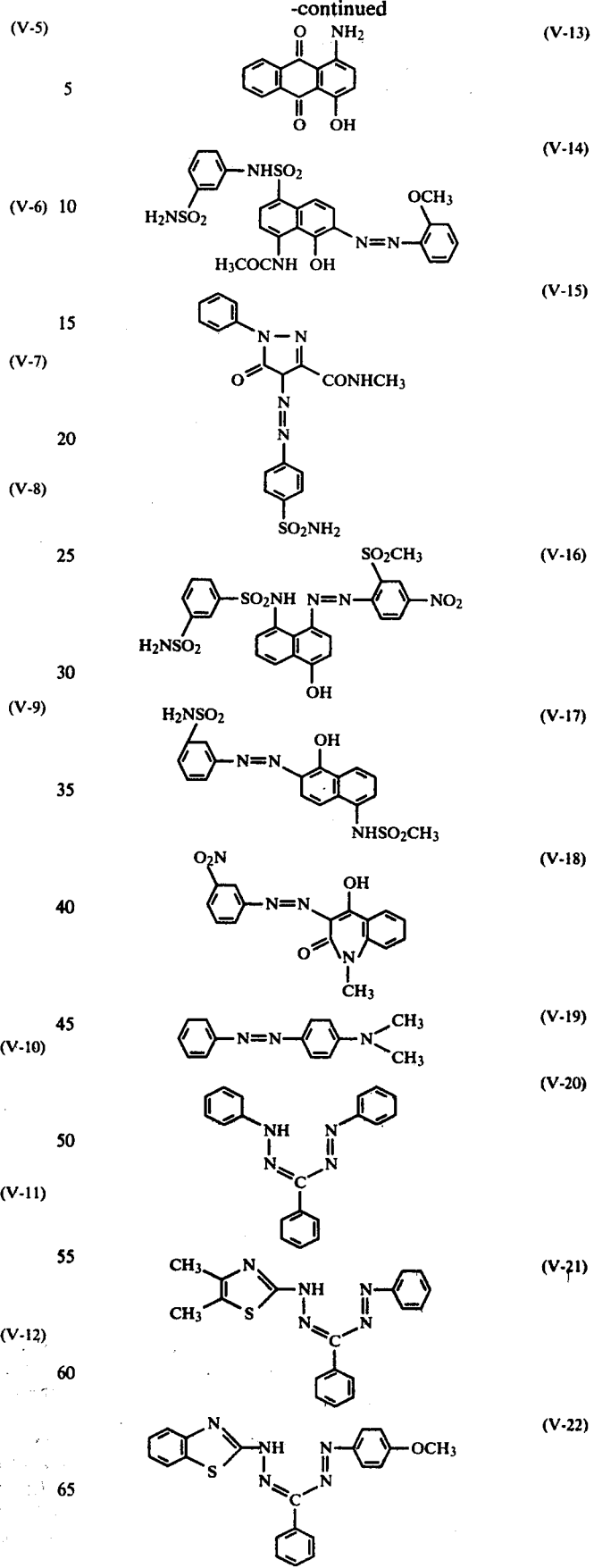

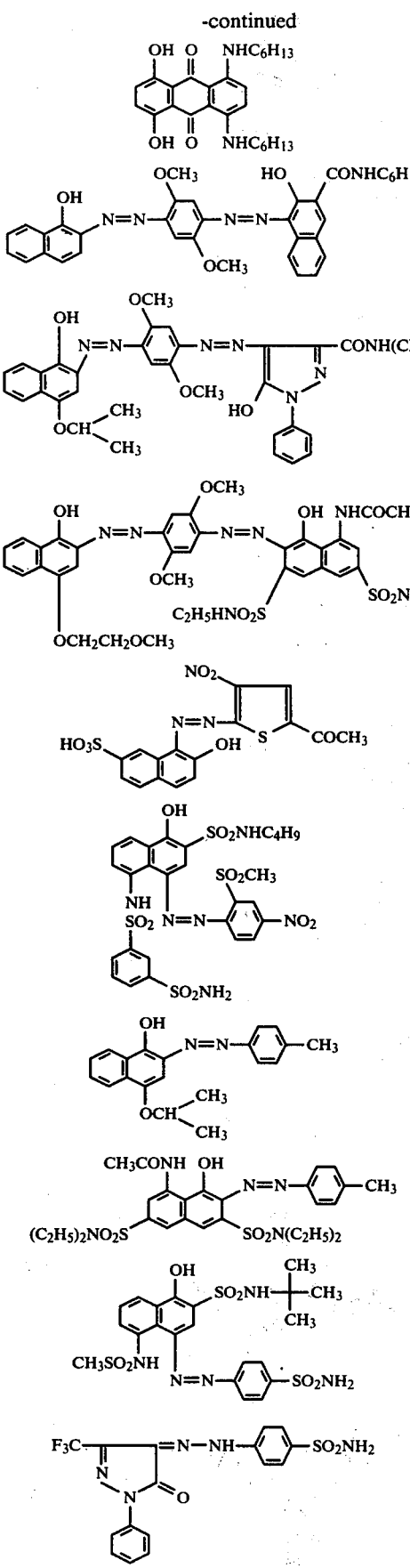
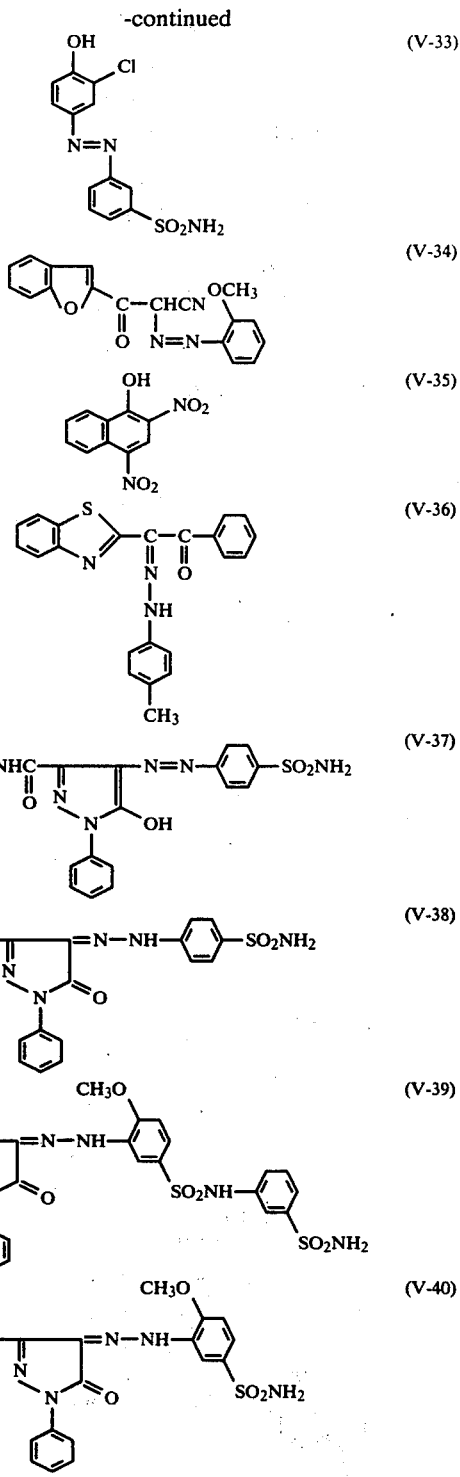
Other types of dyes preferably used in this invention are dyes formed by the oxidation of DRR compounds such as described in U.S. Published Application Ser. No. 351,673, U.S. Pat. Nos. 3,932,381, 3,928,312, 3,931,144, 3,954,476, 3,929,760, 3,942,987, 3,932,380, 4,013,635, and 4,013,633, Japanese Patent Application (OPI) Nos. 113,624/76, 109,928/76, 104,343/76 and 4,819,77, Japanese Patent Application No. 64,533/77 (published as Japanese Patent Application (OPI) No.

149,328/1978) and *Research Disclosure*, 86–74 (1976, Nov.) and *Research Disclosure*, No. 13,024 (1975).

Dyes released by the reaction of an oxidized color developing agent and the DDR couplers also used in this invention are described in British Pat. Nos. 840,731, 904,364, 932,272, 1,014,725, 1,038,331, 1,066,352 and 1,097,064, Japanese Patent Application (OPI) No. 133,021/76, U.S. (U.S. Defensive Publication) T900,029, and U.S. Pat. No. 3,227,550. Still other types of dyes suitably used in this invention are dye developing agents such as described in Japanese Patent Publication Nos. 182/57, 18,332/57, 32,130/73, 43,950/71 and 2,618/74.

Dyes formed in a silver dye bleach process are also suitable for use in the present invention. As yellow dyes used for the purpose, there are azo dyes such as Direct Fast Yellow GC (C.I. 29,000), Chrysophenine (C.I. 24,895), etc.; benzoquinone dyes such as Indigo Golden Yellow IGK (C.I. 59,101), Indigosol Yellow 2GB (C.I. 61,726), Algosol Yellow GCA-CF (C.I. 67,301), Indanthrene Yellow GF (C.I. 68,420), Mikethrene Yellow GC (C.I. 67,300), Indanthrene Yellow GK (C.I. 68,405), etc.; anthraquinone series soluble vat dyes; polycyclic soluble vat dyes; and other vat dyes. As magenta dyes used for the above-mentioned purpose, there are illustrated azo dyes such as Sumilight Supra Rubinol B (C.I. 29,225), Benzo Brilliant Geranine B (C.I. 15,080), etc.; indigoid dyes such as Indigosol Brilliant Pink IR (C.I. 73,361), Indigosol Violet 15R (C.I. 59,321), Indigosol Red Violet IRRL (C.I. 59,316), Indanthrene Red Violet RRK (C.I. 67,895), Mikethrene Brilliant Violet BBK (C.I. 6335), etc.; benzoquinone series soluble vat dyes; anthraquinone series soluble vat dyes; heterocyclic soluble vat dyes; and other vat dyes. As cyan dyes used for the above purpose, there are illustrated azo dyes such as Direct Sky Blue 6B (C.I. 24,410), Direct Brilliant Blue 2B (C.I. 22,610), Sumilight Supra Blue G (C.I. 34,200), etc.; phthalocyanine dyes such as Sumilight Supra Turkish Blue G (C.I. 74,180), Mikethrene Brilliant Blue 4G (C.I. 47,140), etc.; Indanthrene Turkish Blue 5G (C.I. 69,845), Indanthrene Blue GCD (C.I. 73,066), Indigosol 04G (C.I. 73,046), Anthrasol Green (C.I. 59,826), etc.

While the mechanism whereby the complex of the present invention improves light fastness is not entirely clear, it is believed that upon exposure to light the organic substrate (dye image) is excited to a triplet state whereupon the complex interacts with the excited dye to absorb the high energy and thus restore the dye to its original state. Alternatively, oxygen may be excited upon exposure to a singlet state in which case the complex absorbs the high energy of the excited oxygen and restores the oxygen to its original state. In any case the complex of the present invention effectively improves the light fastness of the organic substrate.

As described above, the metal complexes are used in this invention for stabilizing the organic substrate materials. These compounds may be incorporated in one or more silver halide emulsion layers of a color photographic material. Also, these compounds may be incorporated in a layer included in the non-sensitive portion of color photographic transfer materials. The complexes can be supplied for stabilizing photographic images by incorporation into the hydrophilic colloids constituting the photographic layers of a photographic element. The complexes are incorporated as a solution thereof in an organic solvent having low boiling point or an organic solvent miscible with water which does not adversely influence the photographic properties of the photographic layers, such as, for example, an alcohol (e.g., methanol, ethanol, isopropanol, butanol, etc.), an ether (e.g., dimethyl ether, ethyl methyl ether, diethyl ether, 1-ethoxypropane, etc.), a glycol (e.g., 1,2-ethanediol, 1,2-propanediol, 1,3-propanediol, etc.), a ketone (e.g., acetone, ethyl methyl ketone, 3-pentanone, etc.), an ester (e.g., ethyl formate, methyl acetate, ethyl acetate, etc.), an amide (e.g., formamide, acetamide, succinamide, etc.), and the like. It is desirable that the complex be incorporated before coating, such as when producing silver halide photographic emulsions, when forming an emulsified dispersion of couplers, or when preparing photographic coating compositions.

In order to introduce these complexes into hydrophilic colloids constituting photographic layers, methods usually employed for dispersing couplers in the color photographic fields may be employed. In this regard, U.S. Pat. Nos. 2,304,939 and 2,322,027 disclose the use of high boiling organic solvents for dissolving these materials. Other applicable methods are described in U.S. Pat. Nos. 2,801,170, 2,801,171 and 2,949,360, wherein low boiling or water-soluble organic solvents are used together with high boiling organic solvents.

Examples of the high boiling organic solvents which are effective for dispersing the substrate material and metal complexes in this invention are di-n-butyl phthalate, benzyl phthalate, triphenyl phosphate, tri-o-cresyl phosphate, diphenylmono-p-tert-butylphenyl phosphate, monophenyl-di-p-tert-butylphenyl phosphate, diphenyl-mono-o-chlorophenyl phosphate, monophenyl-di-o-chlorophenyl phosphate, 2,4-di-n-amylphenol, 2,4-di-t-amylphenol, N,N-diethyllaurylamide as well as trioctyl phosphate and trihexyl phosphate described in U.S. Pat. No. 3,676,137.

The low boiling or water-soluble organic solvents which can be advantageously used together with these high boiling organic solvents are disclosed in, for example, U.S. Pat. Nos. 2,801,171, 2,801,170 and 2,949,360.

These organic solvents include:

(1) low boiling organic solvents substantially immiscible in water, such as, for example, methyl acetate, ethyl acetate, propyl acetate, butyl acetate, isopropyl acetate, ethyl propionate, sec-butyl alcohol, ethyl formate, nitromethane, nitroethane, carbon tetrachloride, chloroform, etc., and (2) water-miscible organic solvents such as, for example, methyl isobutyl ketone, $\beta$-ethoxyethyl acetate, $\beta$-butoxytetrahydrofurfuryl adipate, diethylene glycol monoacetate, methoxytriglycol acetate, acetonylacetone, diacetone alcohol, ethylene glycol, acetone, methanol, ethanol, acetonitrile, dimethylformamide, dioxane, etc.

In general, the complex of the formula (I) is dissolved or suspended in an appropriate solvent which is chosen depending upon the physical properties of the complex used from water, water-miscible and water-immiscible organic and inorganic solvents (the details of which are described in U.S. Pat. No. 3,966,468) and the organic substrate material is dissolved or suspended therein. Alternatively, again depending upon the physical properties of the compounds, solutions and/or dispersions may be prepared separately and subsequently mixed. For example, a fluorescent whitening agent may be dissolved or suspended in an organic or inorganic solvent such as water or dimethyl formamide, etc., together with the complex of the present invention or separately; and the mixture may be coated onto or incorporated into a suitable base substance. An adjacent double layer coating is possible and in some cases may be preferred if some diffusion between the contiguous layers occurs and light fastness improvement is effected.

The present invention can also be used to improve the light fastness of a colored polymer. A colored polymer is a polymer containing a coloring material in a state of molecular dispersion or melt. The polymer is represented by natural resins other than gelatin, e.g., cellulose and derivatives thereof, vinyl resins, polycondensates, silicone resins, alkyd resins, polyamides, paraffin and mineral waxes as described in U.S. Pat. No. 3,966,468. Where it is desired to improve the light fastness in a colored polymer for use of agricultural vinyl sheets, the colored polymer and complex of the formula (I) are likewise mixed in the form of a solution, dispersion, etc., followed by extrusion molding, etc., in a conventional manner.

In the case of a photographic material, the substrate material (the dye image) and the complex each may be present in one or more of the hydrophilic colloid layers making up a photographic element (e.g., a film, paper, diffusion transfer unit, etc.). It is preferred that the metal chelate complex and the organic substrate material be present (i.e., coexist) in the same emulsion layer, of course, the effects of the present invention can also be attained when the complex and substrate are present in contiguous layers and diffusion occurs between the layers. Where undesirable diffusion occurs, conventional mordanting techniques could be applied to the present invention.

In the case of incorporating the complex into a silver halide emulsion layer, the complex can be incorporated into each emulsion layer making up the photographic element. In this case, the total amount of complex present is in the range set forth below. The complex and substrate may be present in non-light-sensitive elements or layers such as the dye image-receiving layer used in diffusion transfer film units. In the case of image transfer units, the metal chelate complex is preferably located in the layer in which the dye images are finally found, i.e., in an image-receiving layer. Usually, the dye images formed in the image-receiving layer do not diffuse further into any other layer(s) so that the complex is easily maintained in the vicinity of the dye. When the organic substrate material and the complex are incorporated in such a non-photosensitive image-recording or image-receiving element, they are mordanted. The complex contains a ligand capable of retaining it in the mordant layer of the image-receiving element so that it does not diffuse away from the dye stabilized thereby.

A number of types of image transfer film units are particularly appropriate for the practice of the present invention. One is the imbibition transfer film unit set forth in U.S. Pat. No. 2,882,156. The present invention can be further used in conjunction with the color image transfer film unit described in U.S. Pat. Nos. 2,087,817, 3,185,567, 2,983,606, 3,253,915, 3,227,550, 3,227,551, 3,227,552, 3,415,646, 3,594,164 and 3,594,165 and Belgian Pat. Nos. 757,959 and 757,960.

The organic substrate materials and the complexes used in the practice of this invention can be used together with the materials as described in *Product Licensing Index*, Vol. 92, No. 9232, 107–110 (1971, December) according to the manner as described therein.

Any amount of the complex will bring about some improvement in the light fastness of the organic substrate and theoretically there is no upper limit for the amount of the complex. Preferably, the complex is present in an amount of at least 0.1 mol% based on 1 mol of the organic substrate material, more preferably in an amount of 0.1 to 1,000 mol%, and most preferably in an amount of 1 to 300 mol%. In the case of a photographic material, the amount is often expressed in terms of a weight unit per square meter of photographic material which can be calculated from the parameters set out above. In the case of a photographic material, the complex is preferably present in an amount of at least 1 micromole per square meter of the photographic material, and more preferably in an amount of from about 10 to $1 \times 10^4$ micromoles per square meter of the material. The concentration of the substrate material corresponds in general to that for the image forming material usually adopted in color photographic technology. As is well known to those skilled in the art, the substrate material is preferably present in the range of from about 10 to $10^4$ micromoles per square meter of the photographic material. A more preferable range is from about 100 to about $3 \times 10^3$ micromoles per square meter of the photographic product.

The organic substrate material used in this invention generally has a maximum absorption peak in the wavelength region less than about 800 nm. However, the organic substrate material having the maximum absorption peak in the region of from about 300 nm to about 800 nm is preferred and the organic substrate material having the maximum absorption peak in the range of from about 400 nm to about 800 nm is most preferred.

In photographic materials based on this invention, any material ordinarily used as the supports for photographic materials may be used as the support therefor in this invention. Examples thereof are cellulose nitrate films, cellulose acetate films, cellulose acetate butyrate films, cellulose acetate propionate films, polystyrene films, polyethylene terephthalate films, polycarbonate films, laminated sheets of these films, and papers. Also, baryta-coated papers, papers coated with α-olefin polymer, in particular, a polymer of an α-olefin having 2 to 10 carbon atoms, such as polyethylene, polypropylene, etc., and plastic films the surface of which have been roughened to improve their adhesion to other polymers as shown in Japanese Patent Publication No. 19,068/72 are preferably used as the supports for photographic materials.

In photographic materials used in the method of this invention, various hydrophilic colloids are used. Examples of the hydrophilic colloids used as the binders for photographic silver halide emulsions and/or other coating compositions for photographic layers are gelatin; colloidal albumin; casein; cellulose derivatives such as carboxymethyl cellulose, hydroxyethyl cellulose, etc.; sugar derivatives such as agar agar, sodium alginate, starch derivatives, etc.; synthetic hydrophilic colloids such as polyvinyl alcohol, poly-N-vinylpyrrolidone, polyacrylic acid copolymers, maleic anhydride copolymers, polyacrylamide, and the derivatives or partially hydrolyzed products thereof. If necessary, a mixture of two or more of these colloids which are compatible with each other may be used.

Among the aforesaid materials, gelatin is most generally used but gelatin may be replaced partially or wholly with a synthetic polymer. Furthermore, so-called gelatin derivatives, that is, gelatin modified by treatment with an amino group, an imino group, a hydroxy group, a carboxy group, etc., contained in the gelatin molecule as a functional group with a reagent having a functional group which can react with these groups or graft gelatin having bonded thereto the molecular chain of another polymer may be used in place of gelatin.

The silver halide photographic emulsion layers or other photographic layers of photographic materials used in this invention may further contain synthetic polymers such as, for example, water-dispersed vinyl polymers in the form of a latex, in particular, a compound or compounds capable of increasing the dimensional stability of the photographic materials solely or together with a hydrophilic water-permeable colloid.

The silver halide photographic emulsion used in the method of this invention is usually prepared by mixing an aqueous solution of a water-soluble silver salt (e.g., silver nitrate) and an aqueous solution of a water-soluble halogen salt (e.g., potassium bromide) in the presence of a water-soluble polymer solution such as an aqueous solution of gelatin. As such a silver halide, there is silver chloride, silver bromide as well as mixed silver halides such as silver chlorobromide, silver chloroiodide, silver chloroiodobromide, etc. These silver halide grains may be prepared according to a known or conventional processes. As a matter of course, they may be advantageously prepared using the so-called single jet method or double jet method or the controlled double jet method. also, two or more different silver halide emulsions prepared separately may be used in mixture.

The above-mentioned silver halide photographic emulsions may further contain various compounds for preventing a reduction in sensitivity and the formation of fog during production, preservation or processing of the photographic material. As examples of such compounds, there are 4-hydroxy-6-methyl-1,3,3a,7-tetrazaindene, 3-methylbenzothiazole, 1-phenyl-5-mercaptotetrazole as well as many heterocyclic compounds, mercury-containing compounds, mercapto compounds, metal salts, etc.

The silver halide emulsions used in this invention may also be chemically sensitized in a conventional manner. As examples of chemical sensitizers used for the purpose, there are gold compounds such as an aurichlorate, gold trichloride, etc.; salts of noble metals such as platinum, palladium, iridium, and rhodium; sulfur compounds capable of forming silver sulfide by causing reaction with a silver salt, such as sodium thiosulfate, etc.; stannous salts, amines; and other reducing materials.

The silver halide photographic emulsions used in this invention may, if necessary, be subjected to a spectral sensitization or super dye sensitization using cyanine dyes such as cyanine, merocyanine, carbocyanine, etc., solely or as a combination thereof or using a combination of the cyanine dye or dyes and styryl dyes. These dyes are properly selected according to the objects and use of the photographic materials, such as the wavelength region and sensitivity to be stabilized.

The hydrophilic colloid layers of photographic materials used in the method of this invention can be, if necessary, hardened by various cross-linking agents, for example, aldehyde series compounds, active halogen compounds, vinylsulfone compounds, carbodiimide compounds, N-methylol compounds, epoxy compounds, etc.

In applying the method of this invention to color photographic materials, after image exposure, the color photographic material may be processed in a conventional manner to form color images. The main processing steps in such case are color development, bleach, and fix and, if necessary, other steps such as washing and stabilization. In these steps, two or more steps may be performed in one step as blix step. The color development is usually performed in an alkaline solution containing an aromatic primary amine devloping agent. Preferred examples of the aromatic primary amine developing agent are the compounds shown by formulae (A) to (L) described above.

In applying the method of this invention to color photographic materials, wherein the color photographic material is a color photographic diffusion transfer film unit, the processing of the photographic material is carried out automatically in the photographic material. In this case, a color developer containing a color developing agent is contained in a rupturable container. As the developing agent, N-methylaminophenol, 1-phenyl-3-pyrazolidone, 1-phenyl-4,4-dimethyl-3-pyrazolidone, 1-phenyl-4-methylhydroxymethyl-3-pyrazolidone, 3-methoxy-N,N-diethyl-p-phenylenediamine, etc., in addition to the compounds shown by formulae (A) to (L) above are suitable.

For forming color images in photographic materials based on this invention, various known methods can be used, such as the coupling reaction of the above-described dye-forming color couplers and the oxidation product of a p-phenylenediamine series color developing agent; development with a dye developers; the oxidation cleavage reaction of DRR compounds; the dye-releasing reaction upon coupling of DDR couplers; the dye-forming reaction upon coupling reaction of DDR couplers and a silver dye bleaching process.

Accordingly, this invention can be applied to various kinds of color photographic materials such as color positive films, color papers, color negative films, color reversal films, color diffusion transfer film units, silver dye bleaching photographic materials, etc.

The following examples are provided for further understanding of the method of this invention. They are not to be construed as limiting.

EXAMPLE 1

0.1 g of 1-(2,4,6-trichlorophenyl)-3-(2-chloro-5-tetradecanamido)anilino-4-[4-(N-ethyl-N-$\beta$-methanesulfonamidoethyl)aminophenylimino]-5-oxo-2-pyrazoline was dissolved in a mixture of 3 ml of tricresyl phosphate and 5 ml of ethyl acetate. The resulting solution was emulsified by and dispersed into 10 g of a 10% gelatin solution containing 1 ml of a 1% aqueous solution of sodium dodecylbenzenesulfonate. The thus-obtained emulsified dispersion was mixed with 10 g of a 10% gelatin solution and then coated on a paper support both sides of which were laminated by polyethylene films, and dried. (Sample A)

Sample B was prepared in the same manner as Sample A except that Compound I-6 of the present invention was added in an amount of 27 mg (16.2 mg/m$^2$) when the above-described emulsified dispersion was prepared. Samples C and D were also prepared in the same manner as in case of Sample A except that 2,5-di-tert-octylhydroquinone, a conventional fade preventing agent, was added in amounts of 23 mg (13.8 mg/m$^2$) and 230 mg (138 mg/m$^2$), respectively, to the above-described emulsified dispersion.

In each of samples, the coverage of the dye was adjusted to 60 mg/m$^2$. Each of these Samples A to D was subjected to a 48 hour fading test in which it was exposed to light for 48 hours using a xenon tester (intensity of illumination: 200,000 lux) through an ultraviolet filter C-40 (made by Fuji Photo Film Co., Ltd.). The results obtained are shown in Table 1.

TABLE 1

|  | Initial Density | Density after Testing |
|---|---|---|
| Sample A | 0.84 | 0.12 |
| Sample B | 0.86 | 0.65 |
| Sample C | 0.86 | 0.30 |
| Sample D | 0.83 | 0.43 |

Densities were obtained by measurement with a Macbeth densitometer of RD-514 type and a green Status AA filter. The sample B which contained the Compound (I-6) of the present invention faded to a far less extent in comparison to Samples A, C and D. In particular, from Samples C and D, it was confirmed that in spite of the addition of 2,5-ditert-octylhydroquinone in amounts corresponding to the equimolar and ten times the mole concentration of the Compound (I-6) of the present invention, respectively, it was scarcely effective for the prevention of fading. These results demonstrate that Compound (I-6) of the present invention has a striking fade preventing effect.

EXAMPLE 2

Using 0.2 ml of 1 N NaOH solution and 2 ml of methanol, 0.1 g of Compound (V-2) was dissolved. To the resulting solution was added 10 g of a 10% gelatin solution. The thus-obtained dispersion was coated at a coverage of 80 mg of Compound (V-2) per square meter on paper support both sides of which were laminated with polyethylene films. (Sample E)

Sample F was prepared in the same manner as Sample E except that a solution of 31 mg (24.8 mg/m$^2$) of the Compound (I-8) of the present invention in 2 ml of methanol was added to the above-described dispersion just before coating. Sample G was also prepared in the same manner as Sample E except that 18 mg (14.4 mg/m$^2$) of 2,5di-tertoctylhydroquinone, a conventional fade preventing agent for dyes, was added before coating. Each of these samples was fade tested as in Example 1 under 12 hour exposure using an ultraviolet ray absorbing filter. The results obtained are set forth in Table 2.

TABLE 2

|  | Initial Density | Density after Testing |
|---|---|---|
| Sample E | 0.90 | 0.36 |
| Sample F | 0.90 | 0.72 |
| Sample G | 0.92 | 0.49 |

Densities were measured as in Example 1 with a Macbeth densitometer. It is apparent from the results of Table 2 that the Compound (I-8) of the present invention exhibits a very large fade preventing effect.

EXAMPLE 3

0.1 g of a dye having the following chemical structure:

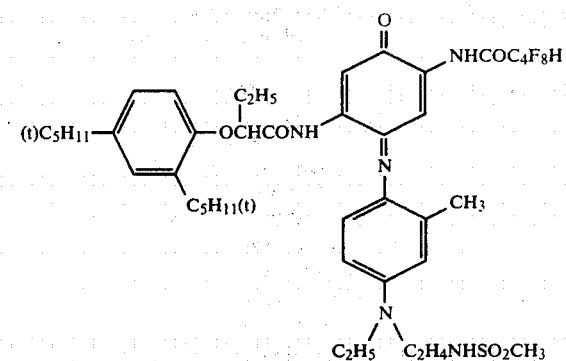

was dissolved in a mixture of 3 ml of dibutyl phthalate and 5 ml of ethyl acetate. The resulting solution was emulsified by and dispersed into 10 g of a 10% gelatin solution containing 1 ml of a 1% aqueous solution of sodium dodecylbenzenesulfonate. Next, the thus-obtained emulsified dispersion was mixed with 10 g of a 10% gelatin solution and then it was coated on a paper support both sides of which were laminated by polyethylene and dried. (Sample H)

Sample I was prepared in the same manner as Sample H except that Compound (I-9) of the present invention was added in an amount of 50 mg (25 mg/m$^2$) during the preparation of the above-described emulsified dispersion. In addition, Sample J was prepared in the same manner as Sample H except that 2,5-di-tert-octylhydroquinone, a conventional fade preventing agent for dyes, was added in an amount of 30 mg (15 mg/m$^2$) to the emulsified dispersion. In each of samples, the coverage of dye was controlled to 50 mg/m$^2$. Each of Samples H to J was fade tested by exposure to light for 48 hours using a xenon tester (illumination intensity: 2,000,000 lux) covered by an ultraviolet ray filter C-40 (made by Fuji Photo Film Co., Ltd.). The results obtained are set forth below in Table 3.

TABLE 3

|  | Initial Density | Density after Testing |
|---|---|---|
| Sample H | 0.83 | 0.23 |
| Sample I | 0.84 | 0.71 |
| Sample J | 0.82 | 0.40 |

Densities were obtained by measurements with a Macbeth densitometer of RD-514 type and the red Status AA filter.

From these results it is seen that Compound (I-9) of the present invention exhibits excellent fade preventing effects. In addition, the compound of the present invention exhibits remarkable effect on cyan dyes, although compounds which are able to effectively prevent fading of cyan dyes have not been known.

EXAMPLE 4

10 g of the magenta coupler of 1-(2,4,6-trichlorophenyl)-3-[(2-chloro-5-tetradecanamido)anilino]-2-pyrazoline-5-one was dissolved in a mixture of 30 ml of tricresyl phosphate, 5 ml of dimethyl formamide and 15 ml of ethyl acetate. The resulting solution was emulsified and dispersed into 80 g of a 10% gelatin solution containing 8 ml of a 1% aqueous solution of sodium dodecylbenzenesulfonate. Next, the thus-obtained emulsified dispersion was admixed with 145 g of green sensitive silver chlorobromide emulsion (Ag content: 7 g, Br content: 50 mol%), and thereto sodium dodecylbenzenesulfonate was added as a coating aid and then it was coated on a paper support both sides of which were laminated with polyethylene. (Sample K). The coverage of the coupler was 400 mg/m².

Samples L and M were prepared in the same manner as the case of Sample K except that 2.8 g (112 mg/m²) of the Compound (I-9) of the present invention and 1.5 g of 2,5-di-tert-octylhydroquinone (60 mg/m²), a known fade preventing agent for dyes, respectively, were added during the preparation of the above-described emulsified dispersion. Each of these samples was exposed to light having an intensity of 1,000 lux for 1 second and then treated successively with the following processing solutions:

Developing Solution:

| | |
|---|---|
| Benzyl Alcohol | 15 ml |
| Diethylenetriamine Pentaacetic Acid | 5 g |
| KBr | 0.4 g |
| Na₂SO₃ | 5 g |
| Na₂CO₃ | 30 g |
| Hydroxylamine Sulfate | 2 g |
| 4-Amino-3-methyl-N-ethyl-N-β-(methane-sulfonamido)ethylaniline . 3/2 H₂SO₄ . H₂O | 4.5 g |
| Water to make | 1,000 ml pH adjusted to 10.1 |

Bleaching-Fixing Solution:

| | |
|---|---|
| Ammonium Thiosulfate (70 wt %) | 150 ml |
| Na₂SO₃ | 5 g |
| Na[Fe(EDTA)] | 40 g |
| EDTA | 4 g |
| Water to make | 1,000 ml pH adjusted to 6.8 |

Conditions of Processings:

| | Temperature | Time |
|---|---|---|
| Developing Solution | 33° C. | 3 min 30 sec |
| Bleaching-Fixing Solution | 33° C. | 1 min 30 sec |
| Washing | 28–35° C. | 3 min |

Each of the samples in which dye image was produced in this way was exposed to sunlight through an ultraviolet ray absorbing filter C-40 (cut off 400 nm, made by Fuji Photo Film Co., Ltd.) for 2 weeks. The results obtained are shown in Table 4. Densities were measured with a Macbeth densitometer of RD-514 type (covered by a Status AA green filter), and the density change was examined in areas having an initial density of 2.0.

TABLE 4

| | Density after Testing | Dye Remnant* (%) |
|---|---|---|
| Sample K | 0.92 | 46 |

TABLE 4-continued

| | Density after Testing | Dye Remnant* (%) |
|---|---|---|
| Sample L | 1.89 | 95 |
| Sample M | 1.27 | 64 |

*((Density after photodeterioration/2.0) × 100)

It is apparent from the above-described results that the Compound (I-9) of the present invention is effective as a photodeterioration inhibitor.

While the invention has been described in detail and with reference to specific embodiments thereof, it will be apparent to one skilled in the art that various changes and modifications can be made therein without departing from the spirit and scope thereof.

What is claimed is:

1. A diffusion transfer color photographic material comprising a photosensitive element and an image-receiving element, said image-receiving element comprising a support having thereon a mordanting layer containing a complex of the formula (I):

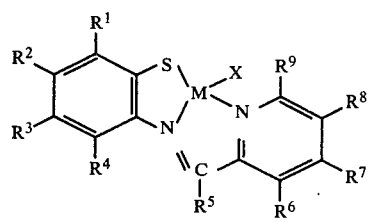

(I)

wherein M represents a Cu, Co, Ni, Pd or Pt atom; $R^1$, $R^2$, $R^3$, $R^4$, $R^6$, $R^7$, $R^8$ and $R^9$ each represents a hydrogen atom, a halogen atom, a cyano group, an alkyl group, an aryl group, a cycloalkyl group or a heterocyclic ring which may be attached to the carbon atom on its respective ring directly or indirectly via a divalent coupling group, or $R^1$ and $R^2$, $R^2$ and $R^3$, $R^3$ and $R^4$, $R^6$ and $R^7$, $R^7$ and $R^8$, or $R^8$ and $R^9$ combine to represent the non-metallic atoms necessary to complete a 6-membered ring; $R^5$ represents a hydrogen atom, an alkyl group or an aryl group; and X represents a chlorine atom, a bromine atom or an iodine atom.

2. The diffusion transfer color photographic material of claim 1, wherein said complex is represented by the formula (Ia):

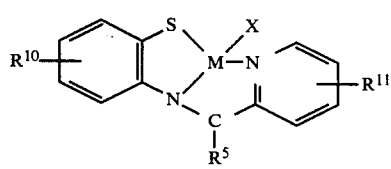

(Ia)

wherein M, $R^5$ and X have the same definition as in formula (I), $R^{10}$ and $R^{11}$ have the same definition as $R^1$ to $R^4$ and $R^6$ to $R^9$ in formula (I).

* * * * *